United States Patent [19]
Medo

[11] Patent Number: 5,902,267
[45] Date of Patent: May 11, 1999

[54] BREAST PUMP SYSTEM USING WALL VACUUM SOURCE

[76] Inventor: Elena M. Medo, 309 Calle Escuela, San Clemente, Calif. 92672

[21] Appl. No.: 08/909,709

[22] Filed: Aug. 11, 1997

Related U.S. Application Data

[60] Provisional application No. 60/023,585, Aug. 9, 1996.

[51] Int. Cl.[6] ..................................................... A61M 1/06
[52] U.S. Cl. ............................... 604/74; 604/35; 604/119
[58] Field of Search .................................. 604/74, 73, 35, 604/118, 119, 120

[56] References Cited

U.S. PATENT DOCUMENTS

| | | |
|---|---|---|
| 1,509,226 | 9/1924 | Brown . |
| 1,670,610 | 5/1928 | Colby . |
| 2,292,401 | 8/1942 | Orre . |
| 2,542,505 | 2/1951 | Gascoigne . |
| 2,652,847 | 9/1953 | Segebarth . |
| 2,669,249 | 2/1954 | Wittmann . |
| 2,991,805 | 7/1961 | Page . |
| 3,183,920 | 5/1965 | Cochran . |
| 3,216,328 | 11/1965 | Peterson . |
| 3,255,776 | 6/1966 | Noorlander . |
| 3,499,465 | 3/1970 | Roop . |
| 3,653,393 | 4/1972 | Love . |
| 3,659,605 | 5/1972 | Sielaff . |
| 3,718,152 | 2/1973 | Kraakman . |
| 3,754,572 | 8/1973 | Scott . |
| 3,812,855 | 5/1974 | Banko . |
| 4,213,457 | 7/1980 | Lewis . |
| 4,303,072 | 12/1981 | Lewis . |
| 4,315,506 | 2/1982 | Kayser et al. . |
| 4,391,294 | 7/1983 | Aubel . |
| 4,573,969 | 3/1986 | Schlensog et al. . |
| 4,600,034 | 7/1986 | Ko . |
| 4,635,681 | 1/1987 | Boldish . |
| 4,747,577 | 5/1988 | Dimock . |
| 4,750,705 | 6/1988 | Zippe . |
| 4,767,403 | 8/1988 | Hodge . |
| 4,772,262 | 9/1988 | Grant et al. . |
| 4,782,849 | 11/1988 | Hodge . |
| 4,794,915 | 1/1989 | Larsson . |
| 4,799,922 | 1/1989 | Beer et al. . |
| 4,813,932 | 3/1989 | Hobbs . |
| 4,819,693 | 4/1989 | Rodder . |
| 5,100,406 | 3/1992 | Panchula . |
| 5,265,638 | 11/1993 | Fischer et al. . |
| 5,578,000 | 11/1996 | Greff et al. . |
| 5,599,308 | 2/1997 | Krupa . |

OTHER PUBLICATIONS

Allied Healthcare Products, Inc. Instruments of Care for Intermittent Vacuum Regulator, Form No. 22–00–3014, Apr., 1989, pp. 1–4.

*Primary Examiner*—John D. Yasko
*Attorney, Agent, or Firm*—Stout, Uxa, Buyan & Mullins, LLP; Donald E. Stout

[57] ABSTRACT

An automatically-modulated breast pump system for connection to a fixed-suction central vacuum system is disclosed. The breast pump system comprises a regulator adapted to be connected to the fixed-suction central vacuum system and adapted to generate a modulated-suction output. The breast pump system further comprises a reservoir adapted to be coupled to the modulated-suction output, and a breast pump flange adapted to be coupled to both the reservoir and a breast of a woman. The modulated-suction output from the regulator is applied to the breast pump flange on the breast to stimulate the breast to generate milk.

19 Claims, 5 Drawing Sheets

BREAST PUMP SYSTEM USING WALL VACUUM SOURCE

This application claims the benefit of U.S. Provisional Application Ser. No. 60/023,585, filed Aug. 9, 1996, which is commonly owned and the contents of which are expressly incorporated herein by reference.

BACKGROUND OF THE INVENTION

1. Field of the Invention

The present invention relates generally to breast pumps and, more particularly, to vacuum-driven breast pumps.

2. Description of Related Art

A variety of breast pump devices have existed in the prior art. Prior art breast pump devices have included non-electric, hand operated suction devices, A/C electrically powered suction devices, battery powered suction devices, and water driven suction devices. Most if not all of these devices have been portable. In a hospital setting where multiple patients typically use the same breast pump, cross-contamination of breast milk can result. Additionally, portable breast pump devices are often transported on trolleys from one patient room to another, further increasing the possibility of cross-contamination of patients at the hospital.

Wall suction systems are commonly built into hospital rooms. Each wall suction system is regulated by a device located at the head of the patient's bed, which is referred to as a regulator. Regulators are traditionally used for purposes of respiratory procedures, wound drainage procedures, and other surgical procedures.

A breast pump system which is adapted to be connected to a valved pipe projecting from a wall is disclosed in U.S. Pat. No. 1,670,610. The device incorporates a rigid cone for accommodating the breast of a user. Use of such a rigid cone, however, has been determined by the present inventor to be painful and less effective in generating the milk-making hormone, prolactin. The suction of this prior art device must be manually modulated by the hand of the user and, accordingly, is limited in efficiency and effectiveness by the skill of the operator. A number of prior art devices have automatically modulated a suction applied to a breast pump device, but these devices have modulated the actual source of the suction (the motor). A device capable of being connected to a fixed-suction source, and capable of automatically modulating a suction from the source, would be useful. No structure is included in the device of the patent for automatically providing modulation of the suction. Nor does the prior art device disclose any means for accurately controlling and monitoring a suction level being applied to the breast of the user. The prior art patent further does not implement any safety relief valves for preventing an accidental application of full-line suction to a woman's breast.

SUMMARY OF THE INVENTION

The automatically-modulated breast pump system of the present invention can reduce or eliminate the prior art problems of cross-contamination of milk and cross-contamination of patients. Since portable breast pumps are not used among different patients with the present invention, the patients and milk from the patients can be isolated from sources of contamination. The breast pump system of the present invention minimizes or eliminates any need for multi-user patient pumping rooms, which have been proven to contribute to harmful flora in newborn nurseries and neonatal intensive care units.

The breast pump system of the present invention is adapted to harness suction from a hospitals' fixed-suction central vacuum system. Portable breast pump devices are, accordingly, generally no longer needed. The breast pump system can provide access to clean, reliable breast pump equipment at the baby's bedside, when the patient is a breast-fed baby or a premature baby who is too small or too sick to breast feed.

The breast pump system of the present invention facilitates breast emptying utilizing the hospital's fixed-suction central vacuum system. A regulator of the present invention can be connected to the mother's central vacuum system connector or the child's central vacuum system connector, and can remain in place for the duration of the patient or the patient's mother stay. The regulator modulates the fixed-suction from the central vacuum system to mimic the suckling of a baby.

A soft breast pump flange is used in accordance with the present invention, to thereby reduce pain and to provide effective generation of milk and production of prolactin. The regulator of the present invention is adapted to automatically modulate the application of suction to the breast pump flange, to thereby mimic the suckling intervals of a nursing baby. Milk production is increased or maximized compared to prior art systems using wall vacuum sources. The present invention further comprises a safety relief valve, for ensuring that accidental full-line suction does not occur. Additionally, means for precisely monitoring and adjusting a level of suction applied to the breast pump flange is provided by the present invention.

According to one aspect of the present invention, an automatically-modulated breast pump system for connection to a fixed-suction central vacuum system is disclosed. The breast pump system comprises a regulator adapted to be connected to the fixed-suction central vacuum system and adapted to generate a modulated-suction output. The breast pump system further comprises a reservoir adapted to be coupled to the modulated-suction output, and a breast pump flange adapted to be coupled to both the reservoir and a breast of a woman. The modulated-suction output from the regulator is applied to the breast pump flange on the breast to stimulate the breast to generate milk.

The fixed-suction central vacuum system can comprise a hospital central vacuum system having a wall connector, and the regulator can be adapted to be connected to the wall connector to thereby connect the regulator to the fixed-suction central vacuum system. The regulator comprises a fixed regulator, which is adapted to receive an input-suction from the fixed-suction central vacuum system and to generate a first output, and an adjustable regulator, which is adapted to receive the first output from the fixed regulator and to generate a second output. The regulator further comprises a modulator, which is adapted to modulate an input-suction from the fixed-suction central vacuum system. In one embodiment, the second output is modulated by the modulator to thereby generate the modulated-suction output. The breast pump flange preferably comprises a Soft Cup Funnel™ breast pump flange, and the regulator preferably comprises a Vacutron™ regulator.

According to another aspect of the present invention, a breast pump system comprises a regulator adapted to be connected to a central vacuum system and to automatically generate a modulated-suction output. The breast pump further comprises a reservoir and a soft breast pump flange. The reservoir is adapted to be coupled to the modulated-suction output, and the soft breast pump flange is adapted to be coupled to both the reservoir and to a breast of a woman.

According to yet another aspect of the present invention, a vacuum-driven, automatically modulated breast pump system for connection to a fixed-suction central vacuum system comprises a non-electric regulator, a reservoir, and a non-electric breast pump flange. The non-electric regulator is adapted to be connected to the fixed-suction central vacuum system and to automatically generate a modulated-suction output, and the non-electric breast pump flange is adapted to be coupled to both the reservoir and to a breast of a woman.

DETAILED DESCRIPTION OF THE PRESENTLY PREFERRED EMBODIMENTS

Figure 1:
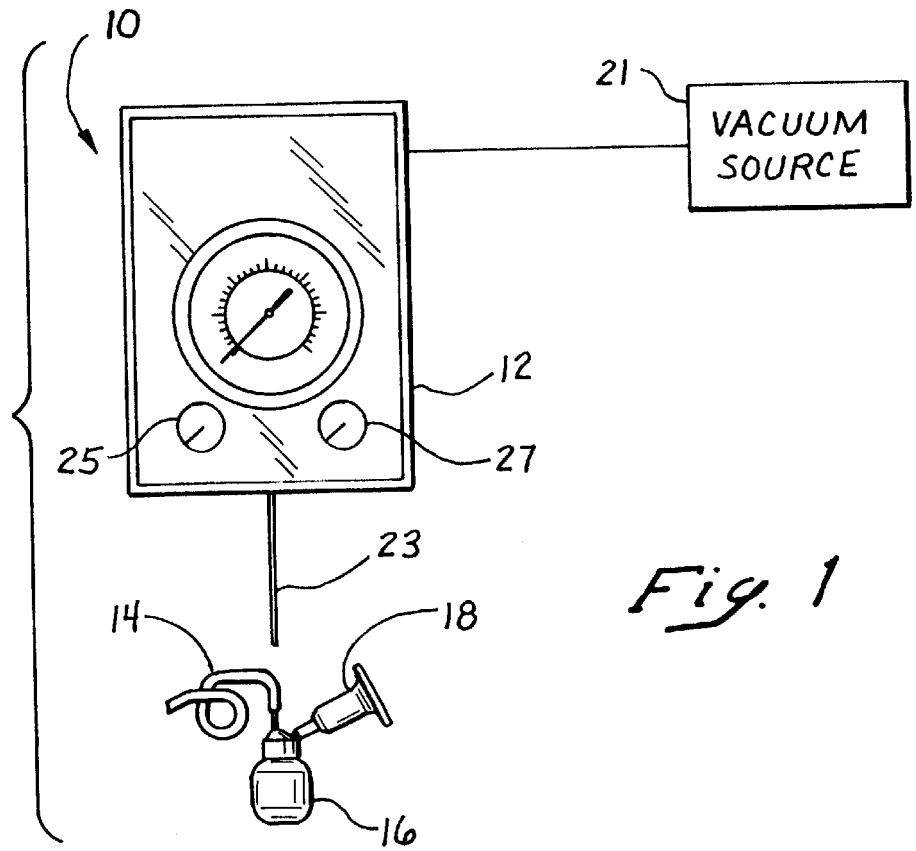
FIG. 1 is a schematic diagram illustrating the breast pump system of the presently preferred embodiment.

Referring more particularly to the drawings, FIG. 1 illustrates a breast pump system 10 comprising a regulator 12, tubing 14, a reservoir 16, and a breast pump flange 18. The regulator 12 is connected to a vacuum source 21, which preferably comprises a hospital central vacuum system. An output line 23 is connected to the tubing 14 of the regulator 12. The regulator 12 preferably comprises a suction level gauge 25 and an on-off switch 27.

Figure 2:
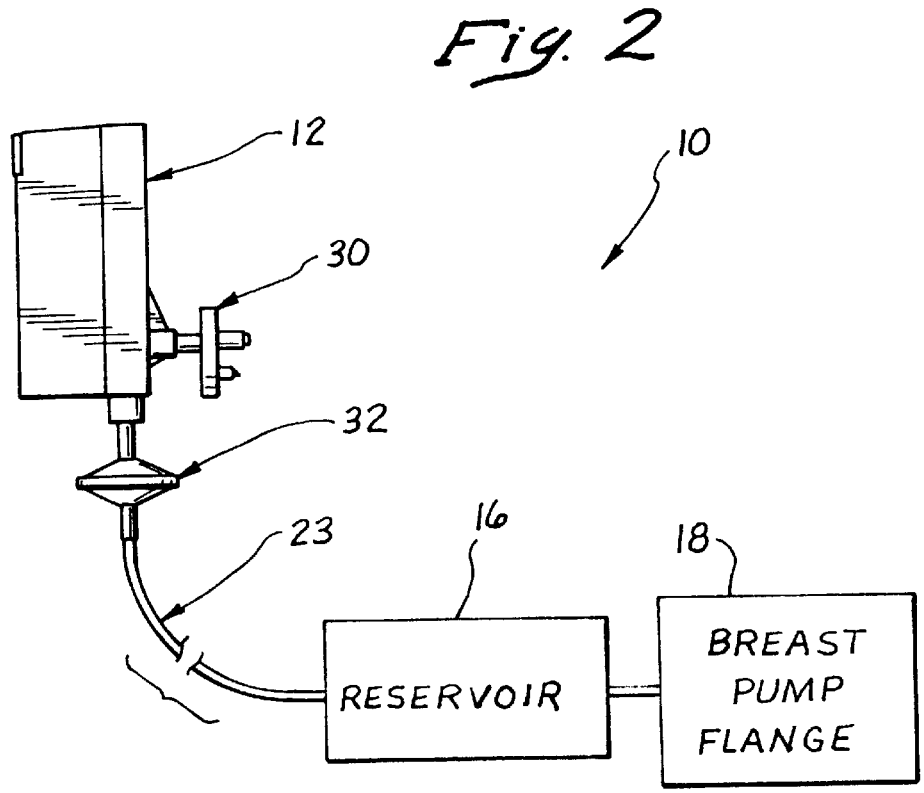
FIG. 2 is a schematic diagram illustrating a side-view of the connection of the regulator to both a vacuum source and a reservoir in accordance with the present invention.

FIG. 2 illustrates a side elevational view of the regulator 12. The regulator 12 comprises a wall connection 30, which is adapted to be connected to the vacuum source 21 via a wall connector (not shown). A bacteria filter 32 is connected between the regulator 12 and the output line 23.

Figure 3:
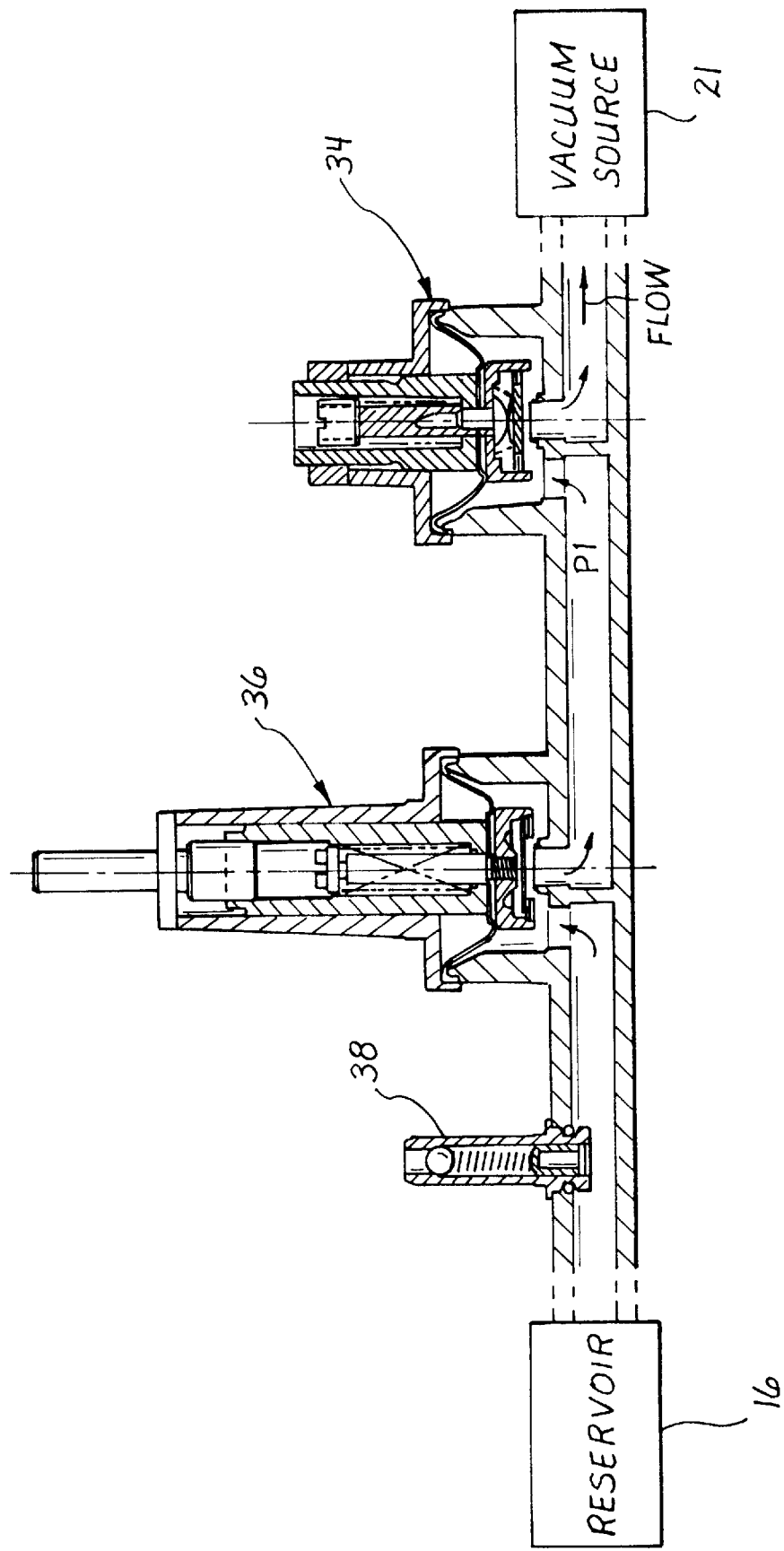
FIG. 3 illustrates a conceptual diagram of the regulator in accordance with the present invention.

FIG. 3 illustrates a schematic diagram of a presently-preferred two-stage regulation system of the regulator 12. A fixed regulator 34 receives a suction from the vacuum source 21, which typically comprises a pressure ranging from 320 to 720 mm HG. The fixed regulator 34 regulates the pressure to a constant pressure within a range of 260 mm HG to 300 mm HG. The fixed regulator 34 provides this regulated pressure to a timing circuit (not shown) of the regulator 12. The pressure from 260 mm HG to 300 mm HG, supplied by the fixed regulator 34, is output to the adjustable regulator 36. The adjustable regulator 36 adjusts the pressure to a range of 0 mm HG to 300 mm HG, depending upon the position of the suction level gauge 25. A safety relief valve 38 is adapted to maintain a pressure output from the adjustable regulator 36 below 300 mm HG. The maximum pressure allowed by the safety relief valve 38 is preferably set within a range of 260 mm HG and 300 mm HG.

The timing circuit (not shown) of the regulator 12 is preferably fixed to provide suction intervals of approximately one second to the breast pump flange 18. In accordance with the present invention, the fixed-suction from the vacuum source 21 is thus regulated and modulated by the regulator 12. As presently embodied, the modulated pressure interval of approximately one second is pre-set and cannot be changed by the user. This modulation interval has been found by the present inventor to achieve optimal production of the milk-making hormone, prolactin, when applied in combination with the breast pump flange 18.

The breast pump flange 18 is driven by the modulated pressure from the regulator 12 and, accordingly, does not require any electrical input. The breast pump flange 18 preferably comprises both a soft material and a configuration optimized to mimic the suckling produced by a nursing baby. As presently embodied, the breast pump flange 18 comprises a Soft Cup Funnel™, and the tubing 14 and reservoir 16 comprise a Breast Pump Kit. Both the Soft Cup Funnel™ and the Breast Pump Kit are manufactured by White River Concepts of San Clemente, Calif. The regulator 12 preferably comprises a Vacutron™ suction regulator, manufactured by Allied Health Care Products of St. Louis, Mo. The configuration, use and literature associated with the Soft Cup Funnel™, Breast Pump Kit, and Vacutron™ products are expressly incorporated herein by reference. An example of a breast pump having a soft breast pump flange is described in U.S. Pat. No. 4,772,262, the contents of which are expressly incorporated herein by reference.

Figure 4:
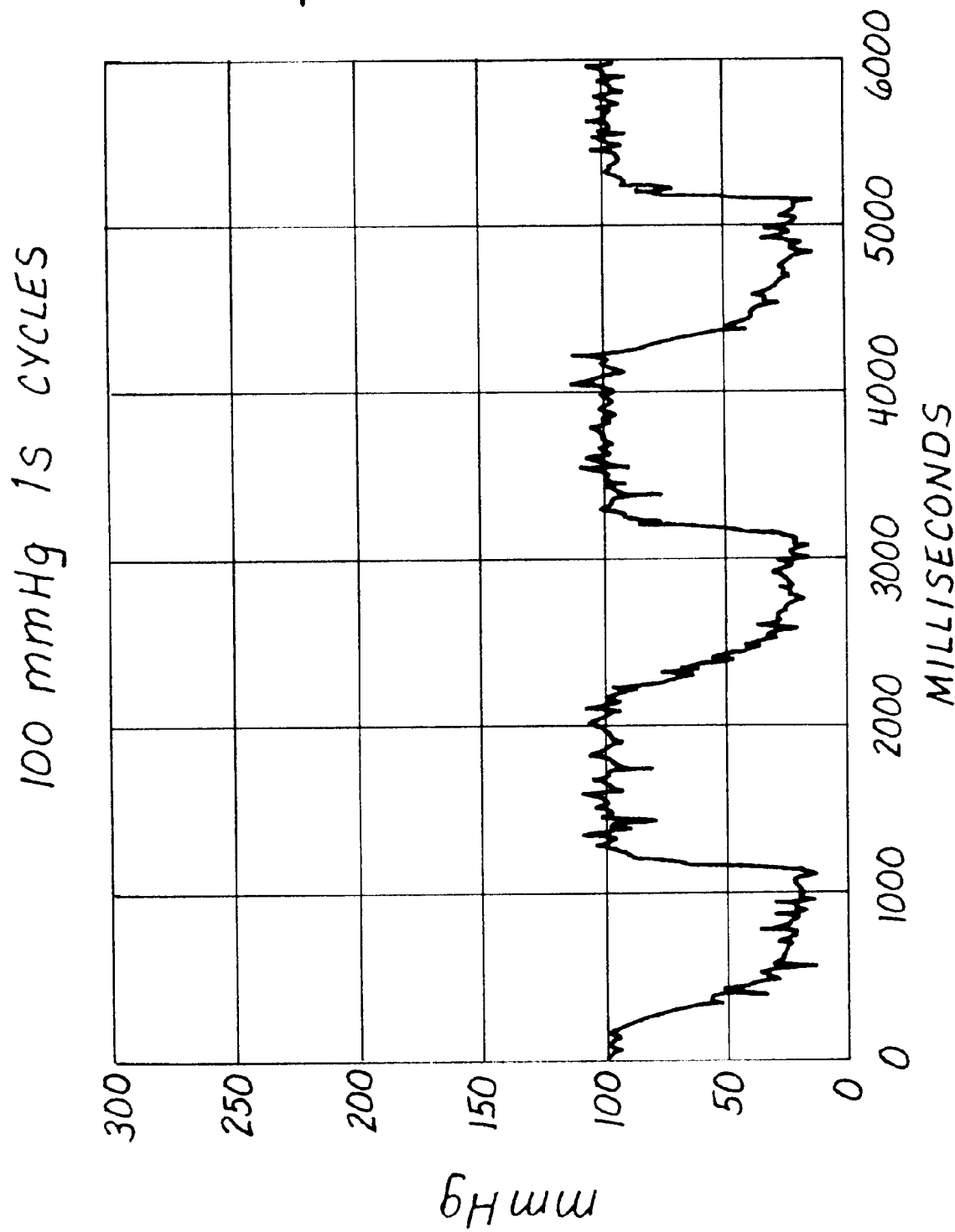
FIG. 4 illustrates a plot of vacuum level versus time for a first configuration of the present invention.
Figure 5:
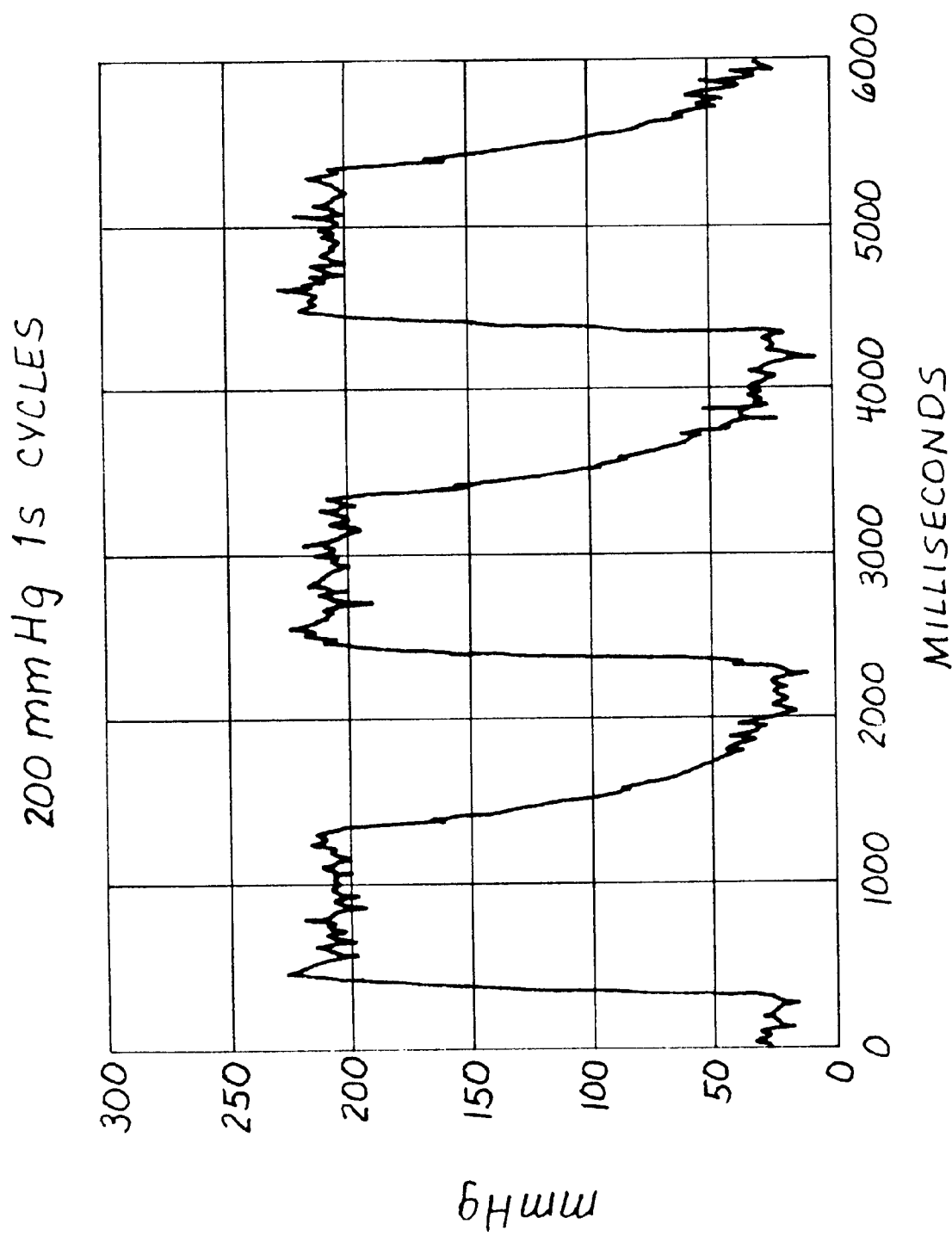
FIG. 5 illustrates a plot of vacuum level versus time for a second configuration of the present invention.
Figure 6:
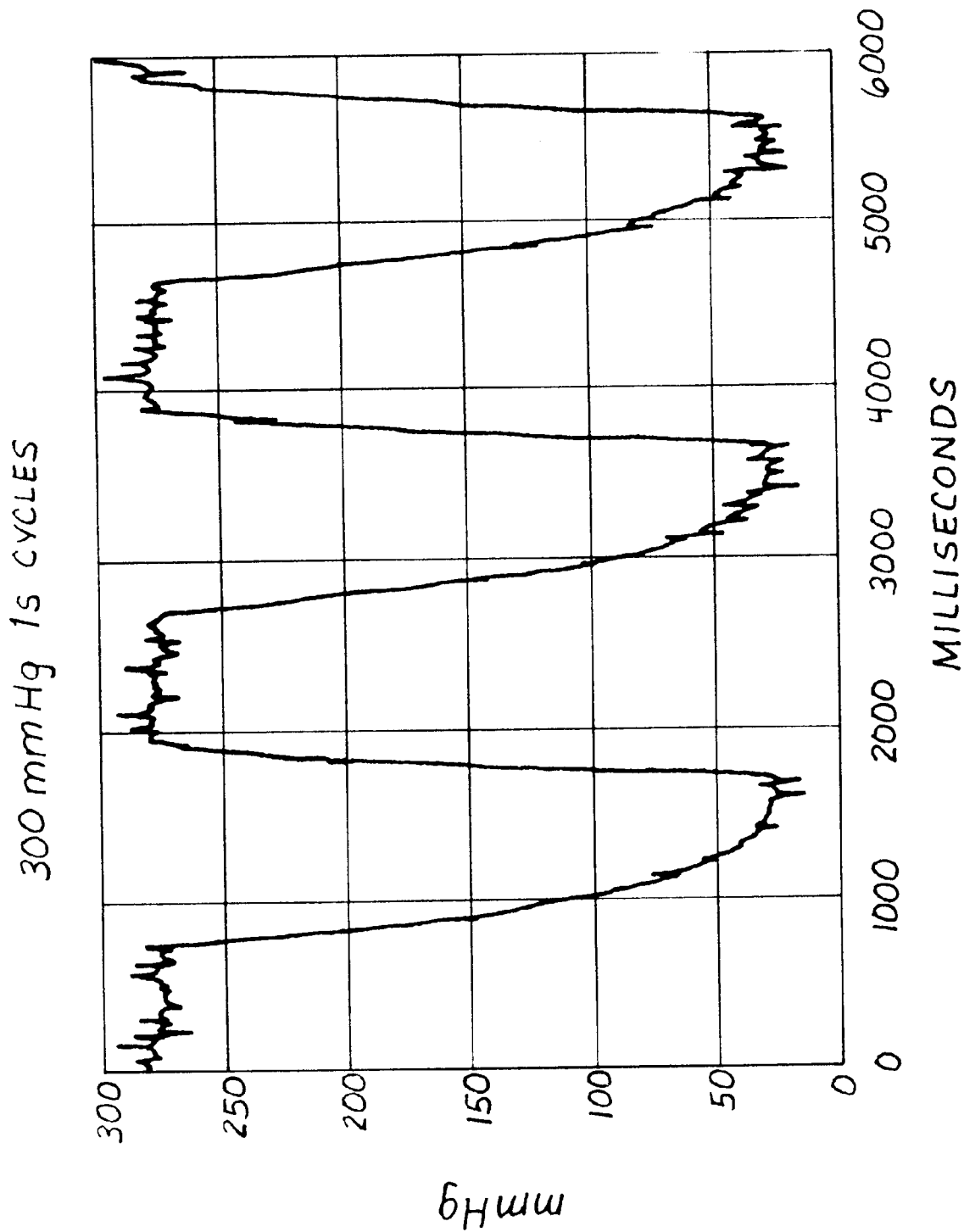
FIG. 6 illustrates a plot of vacuum level versus time for a third configuration of the present invention.

FIGS. 4–6 illustrate plots of pressure versus time, for configurations where the maximum pressures are set to 100 mm HG (FIG. 4), 200 mm HG (FIG. 5), and 300 mm HG (FIG. 6). The settings of 100, 200 and 300 mm HG are set by the safety relief valve 38, and can be set to other desired maximum pressure, according to user preference.

One aspect of the present invention comprises an electronic controller which causes the regulator 12 to perform a series of different suck/release patterns which closely simulate the habits of a nursing baby during an average feeding. By mimicking these patterns, the breast is allowed ample time to refill the ducts after the suck/swallow has occurred. During the beginning of a feeding, the milk is forcefully ejected by the contracting milk-making cells. Very fast sucks with very short pauses result in a large volume of milk being expressed in a relatively brief period of time. As the breast becomes less full, the time needed to refill the ducts increases, due to the effects of the dissipating oxytocin levels. With the decreased oxytocin levels, the milk-making cells begin to relax, and are no longer forcefully pushing milk to the ducts. This is also the time when the baby is beginning to feel sated and has a more relaxed, slower, suck pattern.

By approximating these patterns, the mother is able to stimulate further production of her milk by vigorously stimulating her nipples and emptying more milk in a shorter period of time. This method would also apply to suction at the breast using the wall suction regulator along with a breast cup.

The interface between the wall suction and the lactating breast preferably comprises a soft cone molded in a soft silicone or thermoplastic rubber. The cone latches onto the breast and performs compression patterns which are similar to those of a breastfeeding baby. In order to ensure that compression is accomplished directly over the lactiferous sinuses, an accurate match must occur between the soft cone and the woman's breast. Women's breasts vary in extreme magnitude and so it is a reality that current breastpump technology may not adequately serve a large percentage of women.

According to one aspect of the present invention, an assessment tool enables a nurse or health care provider to correctly fit an appropriate breast pump flange to the individual geography of a patient's breast. The assessment tool facilitates a match between the mother's breast and a soft cone fitting to utilize with the wall suction unit. A three-step assessment results in the selection of the best soft cone of the particular breast features that sometimes make pumping impossible. Nipples come in different lengths, ranging from inverted to one inch long or more. The density of the nipple can also vary, with some nipples easily compressed and others that are dense, and difficult to compress. The lactiferous ducts may be located very deep in the breast, or may be just behind the nipple. When pumping, compression must occur on or behind the ducts, or else no milk will be pumped out. The high number of combinations of the three areas, nipple length, nipple thickness, and nipple density, plus the added variability of the location of the lactiferous ducts, can be addressed by use of the assessment tool of the present invention.

What is claimed is:

1. An automatically-modulated breast pump system for connection to a fixed-suction central vacuum system, comprising:

a regulator adapted to be connected to the fixed-suction central vacuum system and adapted to generate a modulated-suction output;

a reservoir adapted to be coupled to the modulated suction output; and a breast pump flange adapted to be coupled to both the reservoir and to a breast of a woman, whereby the modulated-suction output from the regulator is applied to the breast pump flange on the breast to stimulate the breast to generate milk.

2. The automatically-modulated breast pump system as recited in claim 1, wherein the fixed-suction central vacuum system comprises a hospital central vacuum system.

3. The automatically-modulated breast pump system as recited in claim 2, wherein the fixed-suction central vacuum system comprises a wall connector; and wherein the regulator is adapted to be connected to the wall connector to thereby connect the regulator to the fixed-suction central vacuum system.

4. The automatically-modulated breast pump system as recited in claim 1, wherein the regulator comprises a modulator for modulating an input suction from the fixed-suction central vacuum system.

5. The automatically-modulated breast pump system as recited in claim 1, wherein the regulator comprises:

a fixed regulator adapted to receive an input suction from the fixed-suction central vacuum system and to generate a first output; and an adjustable regulator adapted to receive the first output from the fixed regulator and to generate a second output.

6. The automatically-modulated breast pump system as recited in claim 5, wherein the regulator comprises a modulator which is adapted to modulate an input suction from the fixed-suction central vacuum system.

7. The automatically-modulated breast pump system as recited in claim 6, wherein the second output is modulated by the modulator to thereby generate the modulated-suction output.

8. The automatically-modulated breast pump system as recited in claim 1, wherein the breast pump flange comprises a Soft Cup Funnel™ breast pump flange.

9. The automatically-modulated breast pump system as recited in claim 1, wherein the regulator comprises a Vacutron™ regulator.

10. The automatically-modulated breast pump system as recited in claim 9, wherein the breast pump flange comprises a Soft Cup Funnel™ breast pump flange.

11. A breast pump system for connection to a central vacuum system, comprising:

a regulator adapted to be connected to the central vacuum system and adapted to automatically generate a modulated suction output;

a reservoir adapted to be coupled to the modulated suction output; and a soft breast pump flange adapted to be coupled to both the reservoir and to a breast of a woman, whereby the modulated suction output from the regulator is applied to the soft breast pump flange to stimulate the woman's breast to generate milk.

12. The automatically-modulated breast pump system as recited in claim 11, wherein the central vacuum system comprises a fixed-suction central vacuum system.

13. The automatically-modulated breast pump system as recited in claim 11, wherein the central vacuum system comprises a hospital central vacuum system.

14. The automatically-modulated breast pump system as recited in claim 13, wherein the central vacuum system comprises a wall connector; and wherein the regulator is adapted to be connected to the wall connector to thereby connect the regulator to the central vacuum system.

15. The automatically-modulated breast pump system as recited in claim 11, wherein the soft breast pump flange comprises a Soft Cup Funnel™ soft breast pump flange.

16. The automatically-modulated breast pump system as recited in claim 11, wherein the regulator comprises a Vacutron™ regulator.

17. The automatically-modulated breast pump system as recited in claim 16, wherein the soft breast pump flange comprises a Soft Cup Funnel™ soft breast pump flange.

18. A vacuum-driven, modulated breast pump system for connection to a fixed-suction central vacuum system, comprising:

a non-electric regulator adapted to be connected to the fixed-suction central vacuum system and adapted to automatically generate a modulated-suction output;

a reservoir adapted to be coupled to the modulated-suction output; and a non-electric breast pump flange adapted to be coupled to both the reservoir and to a breast of a woman, whereby the modulated-suction output from the regulator is applied to the non-electric breast pump flange on the breast to stimulate the breast to generate milk.

19. The automatically-modulated breast pump system as recited in claim 18, wherein:

the regulator comprises a Vacutron™ regulator; and the breast pump flange comprises a Soft Cup Funnel™ breast pump flange.

* * * * *